United States Patent [19]

Hafeman et al.

[11] Patent Number: 4,591,550
[45] Date of Patent: May 27, 1986

[54] DEVICE HAVING PHOTORESPONSIVE ELECTRODE FOR DETERMINING ANALYTES INCLUDING LIGANDS AND ANTIBODIES

[75] Inventors: Dean Hafeman, San Bruno, Calif.; John W. Parce, Winston-Salem, N.C.; Harden M. McConnell, Stanford, Calif.

[73] Assignee: Molecular Devices Corporation, Palo Alto, Calif.

[21] Appl. No.: 597,135

[22] Filed: Apr. 5, 1984

Related U.S. Application Data

[63] Continuation-in-part of Ser. No. 585,334, Mar. 1, 1984, abandoned.

[51] Int. Cl.[4] .................... G01N 21/27; G01N 27/07; G01N 33/50; G01N 33/53
[52] U.S. Cl. .......................................... 435/4; 204/1 T; 204/403; 204/412; 324/71.5; 435/7; 435/29; 435/34; 435/39; 435/817; 436/501; 436/806; 436/827
[58] Field of Search ............... 204/1 T, 403, 412; 436/806, 501, 827; 435/7, 29, 34, 817, 4, 39; 324/71.5

[56] References Cited

U.S. PATENT DOCUMENTS

| | | | |
|---|---|---|---|
| 4,020,830 | 5/1977 | Johnson | 204/403 X |
| 4,238,757 | 12/1980 | Schenck | 436/806 X |
| 4,486,272 | 12/1984 | Fujihira | 204/1 T |

Primary Examiner—Sidney Marantz
Attorney, Agent, or Firm—Bertram I. Rowland

[57] ABSTRACT

Photoresponsive devices, including a photoresponsive electrode, are provided and methods for their use to measure changes in environment at a site at or about the surface of the photoresponsive device. By employing a source of light for irradiating a site on the surface and means for biasing the photoresponsive electrode in relation to a counterelectrode, a variation in electrical signal can be related to a change in a medium in photoresponsive modulation relationship to the photoresponsive electrode surface.

38 Claims, 7 Drawing Figures

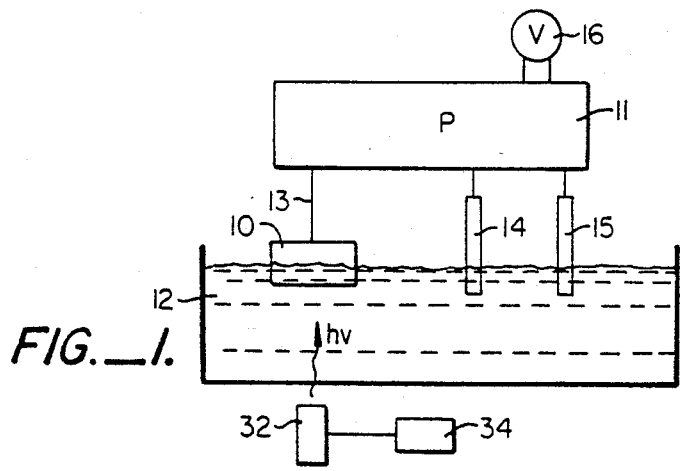
FIG._1.
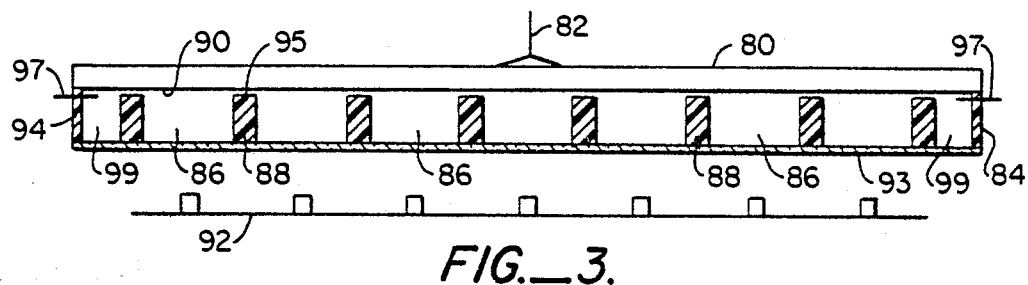
FIG._3.
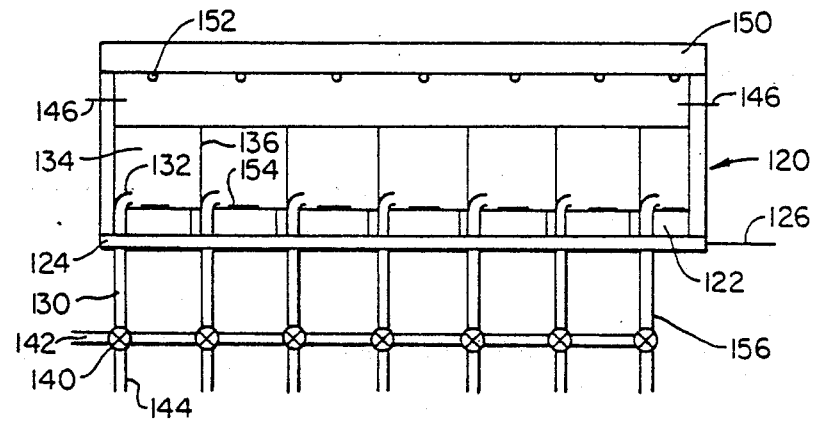
FIG._5.

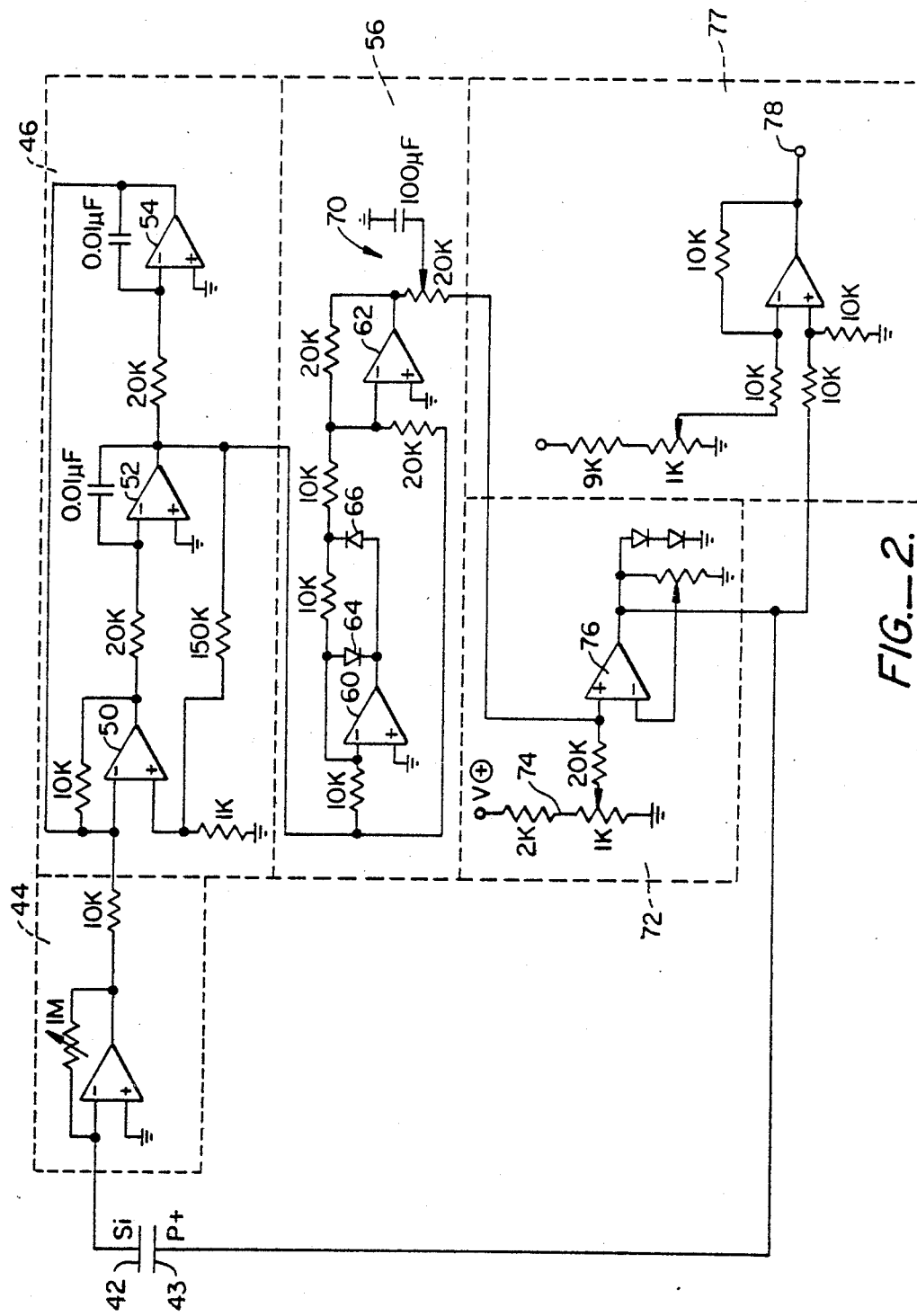
FIG._2.

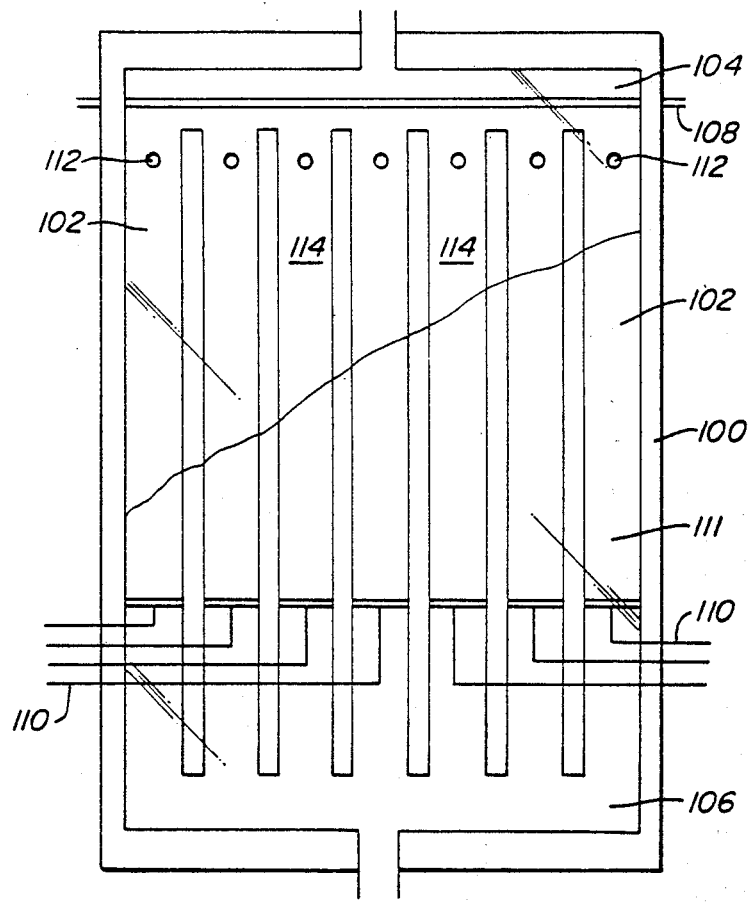
FIG._4.

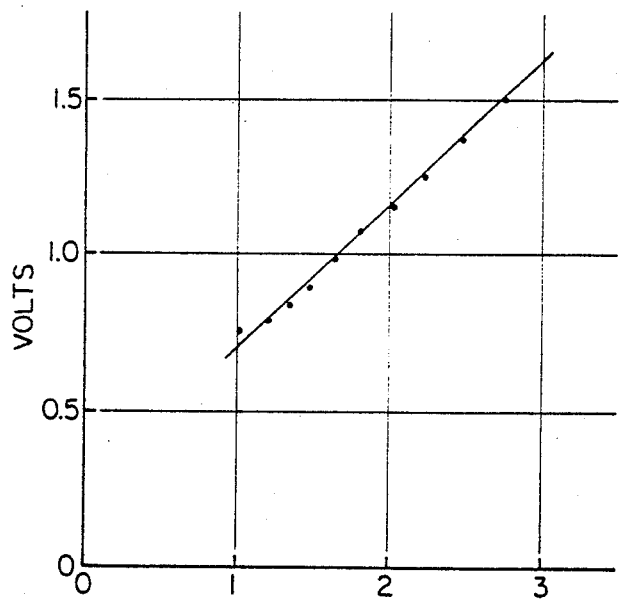
$e^x$, where x is the relative concentration of dye.
FIG._6.
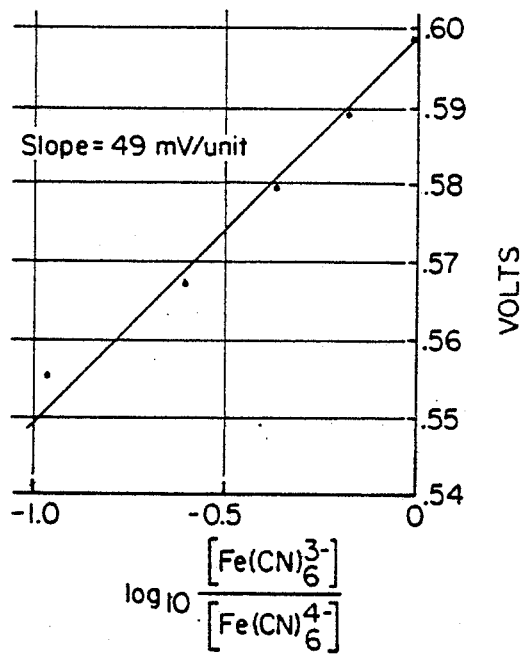
$$\log_{10} \frac{[Fe(CN)_6^{3-}]}{[Fe(CN)_6^{4-}]}$$
FIG._7.

DEVICE HAVING PHOTORESPONSIVE ELECTRODE FOR DETERMINING ANALYTES INCLUDING LIGANDS AND ANTIBODIES

BACKGROUND OF THE INVENTION

1. Field of the Invention

The detection of the presence of a material and/or its amount in a particular environment becomes increasingly important in a society which seeks to monitor and manipulate its environment. Despite the long history of developing devices for measurement of various materials in liquid media, there still remain ample opportunities for improvements in sensitivity, efficiency, economy, and ease of use. Among the manifold detection methods, one device which has found recent application is the field effect transistor (FET) and various modifications of the device. Various studies have been directed to the use of FETs for measurement of organic molecules. See for example, Stenberg et al., *J. Coll. Interface and Sci.* (1979) 72:255-264; Bergveld and De-Rooij, *Med. Biol. Eng. Compt.* (1979) 17:647-654; Bergveld et al., *IEEE Trans. BMI-23* (1976) pages 136-144; and Lauks and Zemel, *IEEE Trans. on Electron Devices,* Vol. ED-26, No. 12 (December 1979), pages 10959-10964. These references are merely illustrative of references directed to semiconductor devices, particularly field effect transistors, for measurement of materials in solution. The FET devices have not found commercial acceptance and in many situations, lack flexibility. For use as chemical detectors, FET devices particularly suffer from the difficulty of obtaining exposed gate regions and working with them in an experimental environment.

As compared to other devices, semiconductive or other devices which respond to an electrical signal provide for a number of advantages. The electrically responsive device can respond to relatively small signals. Furthermore, by various techniques, the signal can be modulated and the background noise diminished or substantially eliminated. Electrical devices can frequently be miniaturized, so that relatively small equipment can be developed for measurement of changes in various fluids.

2. Description of the Prior Art

References of interest include Gronet and Lewis, *Nature* (1982) 300:733-735; Bard and Faulkner, 1980. *Electrochemical Methods–Fundamentals and Applications,* John Wiley and Sons, New York; Fahrenbruch and Bube, 1983. *Fundamentals of Solar Cells–Photovoltaic Energy Conversion,* Academic Press, New York; Fonash, 1981; *Solar Cell Device Physics,* Academic Press, New York; and *Photoeffects at Semiconductor-Electrolyte Surfaces,* ed. Nozik, American Chemical Society, Washington, D.C., 1981. See also U.S. Pat. No. 4,293,310 and PCT Application No. W083/02669.

SUMMARY OF THE INVENTION

Photoresponsive sensing elements, circuits and methods are provided involving measuring electrical signals resulting from irradiation at a plurality of sites, where the signals vary in relation to the environment at each site. A plurality of sites on a photoresponsive surface are irradiated with light of a predetermined wavelength range to produce individually analyzable signals, where each of the signals is related to a medium volume associated with the irradiated site. The photoresponsive surface is polarized in relation to one or more counterelectrodes which is in an electrically transductive relationship through a medium with said photoresponsive surface.

BRIEF DESCRIPTION OF THE DRAWINGS

FIG. 1 is a first exemplary circuit for use in the method of the invention;

FIG. 2 is a second exemplary circuit which provides for the automatic maintenance of the photosignal from a photoresponsive surface at a predetermined value;

FIG. 3 is a diagrammatic cross-sectional view of a photoresponsive device for sampling multiple compartments;

FIG. 4 is a diagrammatic view partially broken away of a manifold for use with the photoresponsive device;

FIG. 5 is a diagrammatic view of a photoresponsive device and an associated sample handling system;

FIG. 6 is a graph of relative concentration of dye in a medium versus voltage response upon irradiation of a photoresponsive surface through a solution of the dye; and FIG. 7 is a graph of observed voltage with varying redox compositions.

DESCRIPTION OF THE SPECIFIC EMBODIMENTS

In accordance with the subject invention, methods and devices are provided which allow for the simultaneous or substantially simultaneous determination of incremental portions of a medium. The device employs a photosensitive sensing element serving as an electrode electrically coupled through a signal analyzing circuit and an electrically communicating medium to at least one counterelectrode. Sites on the photosensitive surface are individually irradiated by light of a predetermined wavelength range, whereby the signals at such individual sites may be individually analyzed. The detectable signal at each of said sites will be related to the level of irradiation at each site and the state of the conduction band within the photosensitive sensing element as a result of the fluid medium adjacent the site on the photoresponsive surface.

The photoresponsive electrode is polarized in relation to at least one counterelectrode. The two electrodes are in electrically communicating relationship, where the medium providing the communicating relationship may be the same as or different from the medium to be analyzed. A circuit is employed which provides for polarizing the photoresponsive electrode with either a reverse or forward bias, where current is either inhibited or allowed to flow through an electrically communicating non-metallic medium, usually a polar fluid medium, e.g., an aqueous medium. Preferably, current flow through the non-metallic electrically communicating medium is inhibited, enhancing the physical stability of the sensing element surface, particularly with a silicon semiconductor. In order to determine the state of an incremental portion of a medium of interest, one irradiates a site in propinquity to said incremental portion and measures the resulting signal as compared to a standard.

The photoresponsive electrode or sensing element or electrode can be a semiconductive material or photoconductive material. Semiconductive materials include such materials as silicon, gallium arsenide, gallium selenide, aluminum gallium arsenide, or the like. The semiconductive material will be either of the p- or n-type and, as appropriate, may employ such dopants as boron, aluminum, phosphorus, arsenic, antimony, or the like. The degree of doping may be varied widely, there being a wide variety of commercially-available doped wafers which can be used. The concentration of the dopant will normally vary empirically to provide the desired photoresponse, frequently being a matter of convenience, and will generally range from about $10^{10}$ to $10^{20}$ atoms/cc; usually for silicon the rating will be about 5–20 ohm-cm. Photoconductive materials include chlorogallium phthalocyanine. Rieke and Armstrong, *J. Am. Chem. Soc.* (1984) 106:47–50.

Various electrical circuits may be used to measure changes in photoresponsiveness of the sensing electrode which result from changes in the state of an incremental portion of the medium. These electrical circuits may primarily measure changes in phototransductance which include photopotential, photoconductance, photocapacitance or photoinductance, or combinations thereof. The circuits will be chosen so as to provide maximal sensitivity for detecting small changes in the state of the medium. These measurements will be generally referred to as the photoresponse.

The observed signal from the circuit can be a result of a change in direct current, alternating current or the effect of a direct current on an alternating current.

Where wafers are used, they may come in a variety of sizes and shapes, varying from chip size which may have its largest dimension of about 0.1mm or wafer size, which may be 100mm, more usually not more than about 75mm in its largest dimension. The device will usually have at least one smooth surface or smooth portion of a surface, desirably flat, which will serve as the irradiation site. The wafer may be round, rectangular, elongate or the like. The thickness of the wafer will generally be not more than about 1mm, usually less than about 2mm, and generally not less than about $0.05\mu$, usually not less than 0.1mm.

The irradiation surface will normally have an associated matrix. The matrix may include a coating of at least about 25Å, more usually at least about 50Å, which may be substantially larger, depending upon its function, usually not exceeding 1000Å, more usually not exceeding 500Å. For the most part, there will be a small amount of a protective oxide or nitride coating or other protective coating, e.g., silicon oxide or nitride.

Alternatively or in combination, the surface may be reacted with a wide variety of organic silanes, particularly halides or esters, which can provide for an organic coating of the surface. The organosilanes will have organogroups of from 1 to 30, more usually of from about 1 to 25 carbon atoms, which may be aliphatic, alicyclic, aromatic or heterocyclic, or combinations thereof, usually hydrocarbon, which may be aliphatically saturated or unsaturated or may be a substituted hydrocarbon having a polar terminus, which may be polar due to: (1) a charge, e.g., carboxylate, phosphate or ammonium; (2) a zwitterion, e.g., betaine; or (3) a dipole, e.g., 3,4-dinitrophenyl, carboxylate ester, phosphate triester, etc.

Where hydrocarbon groups are employed, particularly aliphatic groups of from about 6 to 24 carbon atoms, either saturated or unsaturated, a second layer may be employed to provide for a bilayer membrane. Any lipids may be used for preparing the second layer which provide a stable bilamellar membrane. Alternatively lipids forming stable lamellar membranes may be employed for both layers, avoiding covalent bonding to the surface. Illustrative groups include phospholipids, sphingomyelins, gangliosides, cholesteric compounds, acylglycerols, waxes, and the like.

Conveniently a polymerized lipid bilayer may be employed which may be preprepared and positioned on the surface. See, for example, Wegner, Chapter V, R.A. Welch Foundation Conf. on Chemical Research XXVI Synthetic Polymers, Nov. 15–17, 1982, Houston, TX, which disclosure is incorporated herein by reference. Desirably, the degree of polymerization will be less than 100%, usually from about 20% to 90%, to allow for a substantial degree of fluidity and lateral diffusion. If desired, a first layer may also be employed under the polymerized layer.

Various other materials may be used in conjunction with the surface, which materials may be bound either covalently or non-covalently, or held mechanically in place adjacent to the surface. The materials may be naturally occurring, or synthetic or combinations thereof. These materials include porous films, generally of from about 1 to 50 mil in thickness, normally being polar materials, such as nitrocellulose, partially hydrolyzed polyvinyl acetate, polyacrylates, proteins, polysaccharides, e.g., agarose, etc. Various gels may be used, such as agar, polyacrylamide, or the like. These layers may have independent integrity or rely on the photoresponsive device for support. They will be in direct contact, in whole or in part, with the photoresponsive element, either directly or through intermediate layers.

Various other materials may also be associated with the photoresponsive electrode, which materials will be described in more detail subsequently. Among these may be a confronting spaced apart layer, e.g, sheet or slide. Other materials may be present to provide for specific interactions, particularly complexation between specific binding materials. These materials may be bound directly or indirectly to the photoresponsive surface, particularly to the protective coating, or to the confronting layer.

Any films or coatings or layers should not interfere with the transmission of light of the particular wavelength with which the photoresponsive surface is irradiated. Furthermore, a matrix at the photoresponsive surface may be required to allow for polar interactions as a result of ions or the binding or complexing of polar, particularly charged materials, e.g., proteins, lipids, neuraminic acids, or other charged saccharide, or the like.

The matrix may be of any thickness, so long as it allows for sufficient transmission of light to the semiconductor surface for the desired intensity and for the particular modification of the state of the medium at a site at the surface. The medium employed at the site of the surface will usually allow for diffusion of ions. Therefore, to the extent that solid films are employed, these will usually be porous and immersed in a liquid medium, so as to allow for the diffusion of ions and molecules adjacent the sensing electrode surface to provide for electrical communication between the electrodes.

The device may have a single continuous surface ranging from a surface area of about 1mm$^2$ to about 50cm$^2$, more usually about 25cm$^2$, or in some instances may be a plurality of individual photoresponsive surfaces insulated from each other so as to provide for independent signals to the same circuit. The individual units will usually range from about 0.1mm$^2$ to 5mm$^2$ or greater, the upper limit being primarily one of convenience, although in some situations an enhanced signal may be obtained by employing a large surface area. The individual units may be in contact with media which are partially isolated from each other by the presence of partitions which allow for electrical communication, for example, membranes, fritted walls or partitions extending only a partial distance to the surface, conveniently 25% to 90% of the distance to the surface. Such partitions may also find use with a large photoresponsive surface, as will be described subsequently.

The photoresponsive surface may be divided up physically in a variety of ways, providing for compartments, which may have any convenient periphery, circular, square or the like, channels, which may be circular, serpentine or straight, or combinations thereof. Extended areas such as channels allow for inspection of a moving solution at different times. Channels can be provided by having grooves in the matrix associated with the photoresponsive surface and compartments can be provided for by having indentations in the matrix associated with the photoresponsive surface. The number of independent units to be measured may be 2 or more, usually being 5 or more, and may be 50 or more, and could be as high as 2500.

Alternatively, a facing solid film, layer or plate may be provided, which provides for the appropriate structure, resulting in dividing the photoresponsive surface into compartments and/or channels. The facing surface is normally rigid and may be transparent, opaque, translucent, may be metal, ceramic, glass, or the like. Where translucent or opaque, in relation to the irradiation light, where the facing plate is adjacent to the photoresponsive surface, holes can be provided in the plate for transmission of the light at a variety of sites. Or, optical fibers may be employed for directing light through the plate to particular sites. The plate may be an inert material, merely providing structure, or can be modified by providing for binding of various materials to the surface. These materials would be involved in the determination of the state of an incremental portion of a medium, so as to provide for individual sites which may be individually determined, allowing for the rapid determination of a plurality of results.

Irradiation of the photoresponsive surface may be on either side of the wafer. However, where the irradiation occurs on the side opposite to the side associated with the medium of interest, it will be necessary that the wafer be very thin, so that the conductive band which is influenced by the medium of interest can also be affected by the light irradiation. Normally, in this situation, the thickness of the photoresponsive element will be from about $0.05\mu$ to $2\mu$.

The photoresponsive surface can be influenced by a variety of properties present in the incremental portion of a medium. One property is obviously light absorbence, where the medium may vary in the amount of light absorption. Thus, variations in concentration of a substance which absorbs light in the irradiating wavelength range and is present in the light beam can be detected and measured by the observed signal. In this instance, the incremental portion of the medium of interest may be adjacent or distant from the irradiated site on the photoresponsive surface. Thus, variations in light flux or intensity can be detected and used to measure the amount of an absorbing material in the light beam, where the absorbing material may be the material of interest or the amount of the absorbing material related to a different material of interest.

Other phenomena which provide for a light flux include fluorescence or chemiluminescence. Therefore, irradiation of the photoconductive surface may come from a chemical rather than a physical source. The fluorescence can be as a result of excitation irradiation of a medium, containing a fluorescer, with appropriate light which upon fluorescence results in a light flux to which the photoresponsive element may respond, or a chemical reaction which provides for a fluorescent product by energy transfer. Alternatively, one may have chemiluminescence, where by a chemical reaction, a product is obtained which emits light, e.g., luciferase and luciferin; decomposition of dioxacyclobutanes, etc. Various techniques can be employed whereby the amount of light flux resulting from the fluorescer or chemiluminescer can be modulated in relation to the amount of a material present in the incremental portion of a medium.

Besides variations in light, other phenomena, either chemical or physical, which can affect the photoresponse of the photoresponsive element can also be used to measure the state of the incremental portion. These phenomena include pH, ionic strength, redox potential, or the like. For the most part, these phenomena will require that the incremental portion be at or adjacent to the irradiation site on the photoresponsive surface.

The light source can be any convenient source, particularly of an energy at least about the conduction band gap of the photoresponsive element, so as to produce ion pairs, i.e., free electrons and positive holes. The light source will generally vary in the range of visible to infra-red; for silicon, this is about 1.1eV. This would provide for a wavelength range generally in the range of about $0.1\mu$ to $1\mu$, more usually from about $0.3\mu$ to $1\mu$. Other semiconductors can be matched with a light source accordingly. By employing dyes as a thin layer on the photoresponsive surface, lower energy light may be employed coupled with a redox reaction. The light and dark periods for pulsed radiation may be the same or different, generally ranging from $10^{-2}$ to $10^{-6}$ seconds. The total time of irradiation of a particular site is not critical and may range from $10^{-3}$ to 1 second.

Any source of light may be used which provides the means for providing intermittent light for short periods of time, particularly a source which can provide for cycling the light at a predetermined frequency, e.g., 100Hz–100kHz, usually 100Hz–50kHz, more usually 1–20kHz, during the period of irradiation. Of particular interest are LED arrays, which are available providing red light, or white light, for example, from a tungsten lamp. Alternatively, a single source can be used, e.g., fluorescent light in the visible region; where shutters are used, nematic liquid crystals, gratings, optical fibers, choppers, or the like, may also find application.

Usually, the different sites will be irradiated at different times to provide a simple method for distinguishing between the signals associated with the individual sites. However, simultaneous irradiation of different sites may be employed, where a means is used to allow for distinguishing the signals, such as a phase shift, alternating frequencies, or other combinations where the signals can be segregated.

As indicated above, the subject application can address one or more incremental portions of one or more media to be analyzed, where the incremental portion or volume can be indicative of the gross properties of the medium or particular incremental portions of the medium, where properties of incremental portions may differ in their properties one from the other as well as from the properties of the gross medium. One can inspect incremental portions by irradiating a site on the photoresponsive surface associated with the particular incremental portion. Irradiation at a particular site may be achieved by employing a light source which irradiates the specific site, due to movement of the light source and the photoresponsive surface in relation to one another or by having a plurality of light sources, which irradiate different portions of the photoresponsive surface in accordance with a predetermined schedule, or combinations thereof. In this way, one can address different portions of the medium to determine the state of the incremental portion as to a variety of properties and determine variations in the state of the medium over a large volume. Furthermore, one can employ one or more channels and determine the state of the incremental portions along a channel, so that one can relate variations in the states of the incremental portions along the channel to a temporal change occurring in the medium. By using continuous or intermittent flow techniques, by mixing two media which provide for a detectable reaction prior to entering the irradiation path, one can provide a steady state at each irradiation site along the channel. In this manner, one can determine rates of reaction, by observing the steady state properties of the medium at different sites along a channel.

Thus, the subject invention allows for the substantially simultaneous monitoring of temporal events. Therefore, one can choose to move either one or more light sources or the photoresponsive surface or have a plurality of light sources, which will irradiate a surface in accordance with a predetermined schedule, or, with a plurality of isolated photoresponsive, surfaces have simultaneous irradiation or irradiation at differing times.

Because of the diversity of properties which can be detected, the permissible variations in the conformations which can be employed, and the flexibility in circuitry, a wide variety of different systems and situations can be addressed by the subject invention. While for the most part, fluids providing for modulation of a photoresponsive electrical signal will be monitored, the subject invention allows for monitoring of solid and semi-solids in appropriate situations.

The subject invention can be used for monitoring various streams, such as effluents, natural bodies of water, industrial streams from chemical processing plants, refineries, power generation, and the like, air, or other fluid, where the fluid has a component which will affect a photoresponsive electrical signal or such component can be employed in conjunction with other materials to provide for such a response.

Illustrative of the use of the device is to have one or a plurality of channels between the photoresponsive surface and a transparent metal plate, where the photoresponsive surface and transparent metal plate serve as the plates of a capacitor. The effluent from a Cottrell precipitator could be directed from a number of different sources or the same source through a plurality of channels, where each of the channels could be monitored independently and substantially simultaneously. Where the charge might dissipate with time, by controlling the rate of flow through the channel, one could also determine the rate of dissipation of the charge by monitoring the signal at different sites along the channel.

Thus, the change in the photoresponsive electrical signal in the downstream direction of the channel could be used to determine the rate of charge dissipation.

In another embodiment, one could monitor the change in biological oxygen demand or chemical oxygen demand of an effluent stream or river by having a plurality of channels, which can divide up the stream into numerous individual channels, where different chemicals could be introduced into each individual channel, where the chemical or the product of the reaction provides for modulation of the photoresponsive electrical signal. Where there is a change in light absorption, pH, or other physical phenomenon, the rate of change can be determined by determining the change in electrical signal at different sites along the channel and relating the rate to the chemical or biological oxygen demand.

One can use the subject device for measuring rates of reactions, such as enzymatic reactions, where the enzymatic reaction results in a change in absorbency of the medium, a change in pH or the like. This can be done in a dynamic or static way in that by employing a moving stream, one can make the rate determination substantially instantaneously. Alternatively, by having a relatively static solution at a particular site, which is irradiated intermittently, and readings taken at different times, one can also determine the rate.

The subject invention can also be used with semi-solid or solid media, employing appropriate adaptations. For example, gels can be used for detecting biological transformants, compatible viruses or other situations where one wishes to determine plaques. The method normally involves the growth of a cellular lawn on a nutrient agar and infection with a compatible or unknown virus. Where lysis occurs, a small plaque or clear spot forms. By placing the photoresponsive surface adjacent the gel which will be buffered at a predetermined pH and ionic strength, one can detect the sites where the plaques exist and record those sites by scanning the gel from the opposite side of the photoresponsive surface and detecting variations in light transmission.

Alternatively, frequently cells are transformed with a marker which provides for the expression of an enzyme which reacts with a substrate to produce a color. For example, $\beta$-galactosidase is commonly used, since a commercially available substrate provides for a blue color. As described above, one could grow clones on the surface of a nutrient agar and then automatically screen the clones for the presence of a blue color.

A third situation involving gels may be exemplified by gel electrophoresis of proteins. After performing the electrophoresis, one could contact the gel with a solution of antibody for a protein of interest conjugated to an enzyme which produces a detectable product, for example, an acidic product. After incubating for a sufficient time for any antibody to bind to any protein which is available and diffuses into the gel surface, one could then add a thin layer of substrate and contact the photoresponsive surface with the aqueous layer. Once again, scanning from the reverse side with light would provide for detection of a variation in pH in the medium as a result of the presence of the particular enzyme.

A fourth situation similarly involves electrophoresis of proteins within gels containing a pH gradient. In these techniques, including isoelectric focusing, a pH gradient is set up by artificial means and the rate of migration, or the endpoint position of protein migration within the pH gradient is analyzed. By means of scanning the gel surface with light, similar to the third situation above, both the pH of the gel at various points and the position of the proteins within the gel can be determined.

Instead of proteins, single- or double-stranded polynucleotide sequences may be electrophoresed. Where one uses a restriction endonuclease in digesting a DNA element, e.g., chromosome, virus or plasmid, where the length of the sequence(s) is related to a genetic trait by a particular polymorphism, a plasmid or a viral strain, the subject invention can be used to rapidly determine which polymorphism, plasmid or strain is present. After digestion and denaturing of the DNA sample, ssDNA markers of known length can be used in an adjacent band and the two mixtures electrophoresed. The separated DNA in the gel may then be transferred to a nitrocellulose film and fixed by heating. The fixed DNA may then be probed with a labeled probe under hybridizing conditions. The film is then scanned for the relative relationship of the hybridized dsDNA strands from the sample with the dsDNA strands from the marker by contacting the film with the photoresponsive surface employing an appropriate medium for development of a detectable signal. Light is then directed through the film at different times along the length of the film and the relative separation of the dsDNA segments determined by the signal observed with the device. The spatial relationship of the segments can be used as diagnostic of the presence or absence of a particular DNA element.

Of particular interest will be the use of the subject invention in detecting the presence of a specific component of a medium, where the component may be a chemical, either synthetic or naturally occurring, such as drugs, hormones, proteins, steroids, receptors, nucleic acids, or the like; or aggregations of chemicals, such as nucleosomes, viruses, cells, both prokaryotic and eukaryotic, or the like. These determinations will frequently be made in physiological fluids, such as blood, plasma, saliva, cerebrospinal fluid, lymph, urine, or the like.

The determinations will involve a combination of a ligand and receptor, where the ligand and receptor have a specific affinity, one for the other, so that they provide a pair of specific binding members. Receptors for the most part will be antibodies, enzymes, or naturally occurring receptors, and can for the purposes of this invention include nucleic acids, while ligands may be any compound for which a receptor is available or can be made.

The systems involving specific binding pairs may be varied widely and may involve a "homogeneous" system, where there is no binding to a solid surface or a "heterogeneous" system, where there may be binding, which binding is renewable or non-renewable. By "renewable" is intended that one can remove an active component of the assay system from the surface and replace it with a different component.

For the most part, an aqueous buffered medium will be employed, which may be lightly or heavily buffered depending on the nature of the material generating the signal. Various buffers may be employed, such as carbonate, phosphate, borate, tris, acetate, barbital, Hepes, or the like, at concentrations in the range of about 0.01 to 0.5M. Organic polar solvents, e.g., oxygenated neutral solvents, may be present in amounts ranging from about 0 to 40 volume percent, such as methanol, ethanol, $\alpha$-propanol, acetone, diethylether, etc.

In the specific binding pair assays, there will be a label conjugated to a substance, where the modulation of the photoresponsive signal will be related to the amount of analyte in the sample being assayed. The substance may be the analyte, analyte analog, the complementary binding member or a substance binding to any of these substances. Such substances include antibodies to the immunoglobulin of a species, e.g., sheep antibody to murine immunoglobulin. Also included are pairs, particularly hapten-receptor pairs, where the substance is modified with a hapten, e.g., biotin, and a reciprocal binding member labeled, e.g., avidin. Thus, the label may be bound directly or indirectly, covalently or non-covalently, to a member of the specific binding pair which includes the analyte.

A system is employed which may have one or more components which provides a material in relation to a photoresponsive site which modulates the photoresponsive electrical signal. The manner of modulation may require the material to be adjacent to the photoresponsive surface site, to be in the path of the irradiation light, or other requirement. A substantial diversity of modulating materials may be employed in the specific binding assays, which materials may be the result of a catalyzed reaction, e.g., an enzyme catalyzed reaction.

For the homogeneous system, it will only be necessary that binding result in modulation of an assay system which results in modulation of the photoresponsive electrical signal. The binding can occur adjacent to the photoresponsive surface or distant from the photoresponsive surface, where the photoresponsive surface can be used later to determine the level of the detectable compound in the assay medium. For example, one could carry out a plurality of assays in separate containers, e.g., microtiter plate wells, where a color, e.g., from dyes, is formed in each of the wells in accordance with the amount of an analyte. One could then place the microtiter plate under the photoresponsive surface and by irradiating the different wells at a predetermined schedule, one could rapidly determine the signal for each of the wells. Where light absorbency is involved, it will frequently be desirable to have a relatively long path length. Thus, rather than employing the normal microtiter plate wells, one could employ wells which were relatively deep and have a small diameter, so that the light would pass through a relatively long path length which would include most of the assay medium.

Where products other than dyes are produced which provide for the electrical photoresponse, it will be necessary that there be some electrical interaction with the photoresponsive surface. The electrical interaction can take the form of capacitance or more usually will involve contact with a photoresponsive surface, where the interaction is a result of a change in pH, ionic strength, the redox level of the system, or the like. This can be achieved by having a plurality of wells in which various samples are assayed and then mechanically transferring an aliquot from each of the wells to a designated site on the photoresponsive surface, where the sites are segregated from one another by various means, such as partitions, porous solids, gels, or the like, where each sample has an electrical interaction with a common photoresponsive semiconductor electrode.

For the homogeneous assay, the assay can be carried out adjacent the photoresponsive surface, by having a number of partial partitions extending only a portion of the distance through the assay medium and introducing the sample adjacent the photoresponsive surface. Since the rate of formation of the detectable product will vary with the amount of analyte in the compartment, by comparison of differences between compartments having known amounts of analyte and compartments containing the sample, one can relate the result to the standards. Homogeneous assays include such assays as described in U.S. Pat. Nos. (label) 3,817,837 (enzyme); 3,935,074 (any ligand); 3,996,345 (fluorescer-quencher pairs); 4,160,645 (non-enzymatic catalyst); 4,193,983 (liposome); 4,208,479 (enzyme modifier); 4,275,149 (particles); and 4,341,865 (suicide inhibitors), which appropriate parts are incorporated herein by reference. These patents involve enzymes, fluorescers, redox reagents, and combinations thereof.

For example, there is a commercial assay sold under the trademark EMIT. The assay employs the enzyme glucose-6-phosphate dehydrogenase, which produces NADH from NAD. By providing for an oxidation at the photoresponsive surface, which converts the NADH to NAD, either directly or through the intermediacy of other redox compounds, the rate of formation of NADH by the enzyme may be determined.

The homogeneous enzyme assay employs antibodies to an analyte, where the analyte or an analyte analog is also bound to the enzyme to provide an enzyme-analyte conjugate. When antibody to the analyte binds to the enzyme-analyte conjugate, the enzymatic activity is substantially reduced. Thus, the rate of formation of NADH can be determined and related to the amount of analyte present in the volume adjacent the photoresponsive site.

In carrying out the assay, one could have the photoresponsive site with a plurality of partitions defining a plurality of compartments, where the assay medium extends beyond the partitions. The assay medium would include the enzyme conjugate and buffers, stabilizers, or other additives, which are not directly involved in the system providing for the detectable signal. One would prepare a sample solution containing the antibody, the sample, and appropriate substrates, the mixture incubated, and then injected into the appropriate compartment. The rate of production of a redox reagent, change in pH, or other detectable product could then be followed as indicative of the amount of analyte present in the sample.

Besides having an enzyme conjugated to the analyte or reciprocal binding pair member, one can also conjugate substrates, co-factors, suicide inhibitors, or the like. Various of these techniques are disclosed in U.S. Patents described above. Therefore, one could prepare a conjugate comprising a suicide inhibitor and an analyte. One could bind enzyme, either covalently or non-covalently, to a surface, either the photoresponsive surface or a surface adjacent to the photoresponsive surface. A sample solution would be prepared of antibody to the analyte, the sample, the suicide inhibitor conjugate, substrates, and any additional reagents necessary for producing a detectable product. One could then add the sample solution to the enzyme bound to the surface and determine the enzyme activity. Another homogeneous assay employs an enzyme subunit of a multiunit enzyme, where the subunit can serve as the label. The binding of antibody to the subunit conjugate inhibits the complexing of the subunit to the other units. Alternatively, self-combining protein fragments can be employed. Exemplary of this is the enzyme ribonuclease which is cleaved by subtilisin into the S-peptide and the S-protein, which recombine to form an active enzyme.

The heterogeneous system allows for separation between complexes between specific binding pairs and uncomplexed specific binding pair members. This is achieved by having one of the members of the specific binding pair bound to a solid surface. One could prepare a clear slide having specific antibodies at different sites on the slide, so that one could assay a sample for a plurality of analytes. One would then add antibodies for each of the analytes to the solution, so as to employ a sandwich immunoassay. Conveniently, the antibodies would be monoclonal antibodies to minimize cross-reactivity. One would then add an enzyme conjugate to an antibody which is specific for immunoconjugate globulins from a particular species. For example, if the monoclonal antibodies are murine, one could prepare rabbit antibodies to murine immunoglobulin. Thus, only where the monoclonal murine antibody had bound, would there also be enzyme conjugate. One would then place the clear slide adjacent the photoresponsive surface in registry, so as to define where each of the original antibodies were. A thin, liquid film at the surface would provide the appropriate reagents and substrates for reaction with the enzyme to provide the detectable compound. One would then irradiate the surface sequentially through the clear slide to determine whether any enzyme had become bound at a particular site. In this manner, a sample could be assayed for a large number of different analytes, substantially simultaneously to provide for a complete battery of determinations on a single sample, where extremely small amounts of the sample would be required.

Heterogeneous techniques are described in U.S. Pat. Nos. 3,654,090 (enzyme); 3,791,932 (enzyme); 3,853,987 (fluorescent particle); 3,970,518 (magnetic particle); and 4,134,792 (enzyme substrate), which patents are in appropriate part incorporated herein by reference.

If one wished to repeatedly use the same surface, one could apply a member of a specific binding pair to the surface, where the complementary member is conjugated to a member of a specific binding pair related to the analyte. For example, one could coat the surface with the same or different sugars, haptens, receptors, antibodies, or members of naturally occurring ligand-receptor pairs. One would then conjugate the member of the specific binding pair related to the analyte to the binding member complementary to the material bound to the surface. To illustrate, one could coat the surface with a saccharide and conjugate the analyte related specific binding pair member, e.g., antigen, to a lectin. Thus, one could prepare conjugates of antibodies to a protein analyte and lectins. By adding a solution of the antibody-lectin conjugate to the saccharide-coated surface, the antibodies would become bound to the surface. One could then carry out the assay as described above and after completing the assay, remove the complexed material from the surface by adding a concentrated solution of the saccharide. One can use other pairs by analogy, where in place of a lectin, an antibody or natural receptor could be employed. Thus, a single surface can be used which could be repetitively replenished, so that the same or different types of assays may be employed after each determination. By binding different compounds to the surface at different sites, one can direct specific binding pair members to a specific site with the appropriate conjugate.

Various techniques may be used with enzymes for amplification and enhanced sensitivity. pH cascades can be employed, by employing enzymes having different pH optima. By having the bulk solution at a pH for one enzyme, which produces a product which can provide a different pH in a localized environment, which is the optimum for a second enzyme, which produces a product which further changes the pH in the same direction, one can provide for localized enhancement or amplification. Similarly, one may employ enzymes which require coenzymes or substrates which can be produced by another enzyme. In the example given above, one could bind a first enzyme to the slide and have the second enzyme conjugated to the receptor. Thus, the first enzyme could provide for a high localized concentration of the substrate or co-enzyme for the second enzyme. Illustrative enzyme pairs include glucose oxidase and horseradish peroxidase to produce a densely colored product, a kinase and G6PDH, which with glucose and NAD can produce NADH, which may then be coupled with INT dye, etc.

Catalysts other than enzyme catalysts may be used, particularly redox catalysts. These catalysts may include such compounds as phenazine methosulfate, methylene blue, nicotinamide adenine dinucleotide, Meldola blue, flavin mononucleotide, ferri- and ferrocyanide, and the like. These compounds may be used in conjunction with enzymes or other catalytic compounds to provide for a redox potential at the semiconductor surface. For example, instead of conjugating receptors with enzymes, one could conjugate receptors with phenazine methosulfate, Meldola blue, methylene blue, etc. By then employing the couple of NADH and a tetrazolium salt, an intense color could be produced at the surface.

Redox reagents can be coupled with naturally occurring enzyme transport systems involving cells, membrane fragments, or individual members joined in vitro or disassociated in the medium. Thus, amplification can be achieved. Alternatively, the presence of intact cells or cell fragments can be detected by their influence on a redox couple.

In many situations it will be of interest to determine the presence of a natural receptor in a physiological fluid, particularly blood or plasma. Usually, the receptor will be an antibody, resulting from an autoimmune disease, foreign substance, or an infection. The antibody may be detected in a competition assay, where the endogenous antibody competes with labeled antibody for the complementary antigen or the antibody may serve as a bridge to bind labeled antigen to antigen bound to a surface or particle. Otherwise, for the most part, the antibody assay would follow the techniques employed for detecting antigens.

In some situations it may be desirable to have lipid mono- or bilayers covalently or non-covalently bound to the photoresponsive surface or other surface which can be brought in proximity to the photoresponsive surface. A single lipid layer may be formed by employing aliphatic silyl halides or esters, where the silyl compound may have from one to three aliphatic chains, generally of from about 12 to 24 carbon atoms, more usually of from about 12 to 20 carbon atoms. In addition, other materials may be present, either bonded to a silyl group or bonded to the aliphatic chain, including aryl groups, functionalities, e.g., carboxyl groups, halo groups, amino groups, or the like. One can then provide for the second layer by dipping the surface through a lipid monolayer and then raising the surface horizontally, so that the second layer forms on the first layer to form a bilayer.

A wide variety of lamellar-forming lipids may be employed, particularly phospholipids used in the formation of liposomes and the like. Alternatively, a bilayer may be formed by plasma cleaning of the particular surface, passing the wafer vertically through the monolayer and pulling the wafer out at a speed slow enough to permit water to drain from the surface. The wafer is then pushed through the monolayer horizontally, followed by covering with a cover slip.

The bilayers allow for lateral diffusion within the layer. One can provide for various groups bound to lipids which will specifically bind to an analyte, e.g., antibodies. One could provide for the presence of fluorescers and quenchers bound to antibodies which are specific for different antigens on a cell surface. The presence of the cell will bring together the quenchers and fluorescers which would inhibit any fluorescence upon excitation of the bilayer. Where the light emitted by the fluorescer approximates the energy of the conduction band gap, and, particularly, where the light used for excitation is parallel to the photoresponsive surface, the amount of light which strikes the surface will be related to the presence or absence of a cell having the antigenic sites associated with the antibodies bound to the bilayer. It is not essential that the light be parallel to the photoresponsive surface, it being sufficient that it either be normal to or at an angle, where there is a substantial diminution in signal when the cell having the complementary antigenic sites is present and binds to the antibodies present in the bilayer resulting in quenching.

The use of bilayers can also be coupled with ionophores as labels, where the ionophores allow for transport of ions through the bilayer to the photoresponsive surface. Thus, ionophores may be coupled to specific binding partners, e.g., ligands or receptors which would specifically bind to their complementary partner bound to the bilayer. The presence of the free ionophore would modulate the photoresponse due to the enhanced concentration of ions in close proximity to the surface. Illustrative ionophores include mellitin, nonactin, valinomycin, alamethicin, crown ethers, and the like.

Besides haptens, proteins and saccharides, nucleic acids can also be detected by the subject method. Nucleic acids, either RNA or DNA, can be detected by hybridization with probes having complementary sequences in a competitive or non-competitive manner. In a competitive manner, a nucleic acid sequence may be bound to a surface. A sample suspected of containing the complementary sequence may be combined with a labeled complementary sequence, e.g., labeled with biotin. The mixture is then combined with the surface bound polynucleotide under hybridization conditions and non-specifically bound oligonucleotides removed. Enzyme-avidin conjugate may then be added, where the avidin binds to any biotin present. The presence of specifically bound enzyme may then be detected in accordance with the ways described previously.

Alternatively, a sample containing a plurality of microorganisms may be spread on an appropriate nutrient agar gel and cloned. Employing the Grunstein-Hogness technique, cells are transferred to a nitrocellulose porous film in appropriate registry with their position on the gel, lysed and the DNA fixed to the film by heating. Probes having a complementary sequence to a unique sequence of the organism of interest are provided as partial single strands with a double-stranded 3'-terminus having a sequence specifically recognized by a protein, e.g., repressor, rho, N protein of lambda, or the like. The film is contacted with the probe under hybridizing conditions, e.g., 50% aqueous saline dimethyl formamide and the hybridization solution then removed. After washing the film a solution of the specific binding receptor may be labeled with a plurality of catechols. After sufficient time for the labeled protein to bind, the film is washed free of non-specifically bound protein and placed in close-facing juxtaposition to the photoresponsive surface. A boric acid solution is then added and the pH determined at individual sites associated with each clone by irradiating each clone. The acidity of the complexed boric acid distinguishes the presence of the microorganism of interest.

The microorganisms can also be used to measure the presence of a biostat or biocide in a medium. By combining the medium with growing microorganisms and determining the rate of growth of the microorganisms as compared to a standard differing only in the absence of the medium the presence of a biocide can be detected. By employing immortalized mammalian cells, e.g., tumor cells, the presence of growth regulators can also be detected.

Finally, the rate of flow of a medium can be determined by determining the streaming potential, e.g., tribovoltaic effect.

The following examples are illustrative of the manner in which the subject methodology could be used. The device, either a single surface or a plurality of individual non-contiguous surface units, has partitions to isolate individual areas or compartments. A film is employed proximate to the surface having lectins specific for a particular mono- or oligosaccharide. Antibodies are modified with the particular saccharide and antibodies for the same or different ligands are introduced into each compartment and the excess washed away. A sample is now introduced which overflows the compartment partitions and any complementary ligand becomes bound in the appropriate compartment. The sample is then washed away and an antibody mixture added which binds to the single or multiple ligands bound to the antibodies in the compartments. These antibodies are all from a single source, e.g., mice. The antibody solution is washed, a conjugate of an enzyme with rabbit antibody to mouse immunoglobulin is added and allowed to overflow the compartment walls and bind to any mouse immunoglobulin in the compartments. The non-specifically bound enzyme may then be washed away and the enzyme activity in each compartment determined by adding a substrate medium to each compartment which provides a product which can be photoresponsively determined, e.g., pH change, color absorbency, etc.

A different technique would involve a gel where different antibodies are present at about 2mm intervals. The gel is made with a salt solution and is in contact for electrical communications with a salt solution. The gel is then contacted with the sample which contains conjugates of ligands of interest, where the label is a long-lived fluorescer, e.g., a europium chelate. The amount of the fluorescer present at each site on the gel will be inversely proportional to the amount of ligand present. After removing any non-specifically bound fluorescer, the individual sites are irradiated and the signal observed after the irradiation has stopped and the fluorescent light is emitted.

In another embodiment, individual photoconductive units are provided having antibodies covalently bonded to the surface of each unit through a silyl-substituted aliphatic carboxylic acid. The sample is then contacted with the antibody, the sample washed away and enzyme-conjugated-antibody added. After sufficient time for binding, non-specifically bound enzyme is removed and a developer solution added which produces NADH. The amount of NADH produced by the enzyme can be indirectly reoxidized by the photoresponsive electrode so that the NAD may be recycled. The rate of formation of NADH is related to the photoresponse as a result of photooxidation.

Various circuits may be employed for determining the state of the medium adjacent the surface. Besides the photoresponsive sensing electrode, there will be at least one counterelectrode, preferably two counterelectrodes, and there may be a counterelectrode for each compartment or channel of the device. The same or different electrode may serve as a controlling or reference electrode.

Various electrodes of a variety of materials may be used, so long as the materials of the electrode do not adversely affect the photoresponsive electrode, are not adversely affected by, and preferably not sensitive to the electrically communicating medium, and do not adversely affect the electrically communicating medium. Illustrative electrodes include such materials as platinum, rhodium, palladium, silver-silver chloride, calomel, conducting glass electrode ($SnO_2$, $InO_2$ or ITO), etc. In some instances it may be desirable to encase the electrode in an electrically communicating shield, e.g., gelatin.

In one embodiment, there are three electrodes, the sensing electrode, a reference electrode and a controlling electrode. The potential between the sensing electrode and the reference electrode can be varied by varying the potential applied to the controlling electrode with respect to the sensing electrode. The light emitting diode or other light source is powered with an external electronic circuit so as to emit light which varies in a regular pattern, e.g., square-wave, sine-wave, etc., in intensity with time, resulting in a time dependent response of the sensing electrode, which can be detected by measuring the current through the controlling electrode required to maintain a constant potential between the sensing electrode and the reference electrode.

In this configuration the peak to peak amplitude of the periodically varying current through the controlling electrode varies as a function of the chemical environment at the sensing electrode and as a function of the potential applied between the sensing electrode and the controlling electrode. This configuration can be further simplified by shorting together the leads to the controlling and reference electrodes and removing the reference electrode from the circuit.

Turning now to FIG. 1, the semiconductor electrode 10 is positioned at the surface of an aqueous medium 12. Lead 13 and potentiostat 11, e.g., Model 363 Potentiostat/Galvenstat PAR (Princeton Applied Research), connect the semiconductor electrode 10, the reference electrode 14 and the controlling electrode 15. The potentiostat 11 supplies a polarizing current through the controlling electrode 15 and sensing electrode 10, which maintains a constant potential between the sensing electrode and the reference electrode 14. The current required to maintain a fixed potential between electrodes 10 and 14 is recorded as a voltage on meter output 16. An LED 32 is controlled by pulse circuit 34 to emit regular pulses of light at a predetermined frequency.

Another circuit which may be employed involves automatically varying the potential between the controlling and sensing electrodes so as to maintain a constant amplitude sinusoidal current through the controlling electrode in response to sinusoidal irradiation of the sensing electrode. Turning now to FIG. 2, the circuit has depicted a silicon wafer 42 which serves as the sensing electrode and a platinum electrode 43 which serves as the controlling electrode. (Resistors and capacitors will not be specifically mentioned, although depicted in the figure.) An operational amplifier 44 converts the current passing through the controlling and p-doped silicon semiconductor electrodes to a voltage and feeds the signal to a bandpass amplifier 46, which is comprised of three operational amplifiers 50, 52 and 54. The signal from the bandpass amplifier 46 is fed to the precision rectifier 56 which includes two operational amplifiers 60 and 62 as well as two diodes 64 and 66. A variable filter 70 is provided to smooth out the rectified signal and determine the response time of the circuit to changes in the chemical environment at the silicon electrode. A negative signal is fed to the controlling amplifier 72 which includes potentiometer 74 and operational amplifier 76. The controlling amplifier serves to control the potential at the platinum electrode 43. The negative signal fed to the controlling amplifier 72 is related to the amplitude of the alternating current through the Pt and Si electrodes in response to the sinusoidal irradiation of the Si electrode 42. For recording, the signal from the controlling amplifier 72 is fed to a unity gain amplifier 74 which allows for control of the base value for the recorder. Thus, as different sites are irradiated with regular sine-wave pulses on the silicon wafer surface, the recorder will respond with the reading of the potential between the Pt and Si electrodes necessary to maintain a constant amplitude alternating current through the Pt and Si electrodes. This circuit is referred to as CAM for constant amplitude module. Circuitry not shown provides for sinusoidal light irradiation of the wafer in accordance with a predetermined schedule.

A third general circuit which may be employed involves automatically varying the peak to peak amplitude of the LED output so as to maintain a constant photoresponse of the sensing electrode at a constant potential between the sensing and controlling electrodes. In this configuration, the detected signal which is sensitive to the environment at the sensing electrode is the peak to peak current passing through the LED.

Where capacitance is employed as the electrical response, the change in capacitance can be determined in relation to a change in current resulting from a change in capacitance in the assay medium.

FIG. 3 shows a cross-section of an exemplary device having silicon wafer 80 connected to a circuit by wire 82 and mounted in container 84. Container 84 has a plurality of compartments 86 in which different assay samples are present. The compartment walls 88 would generally be of about 0.5 to 5 mm in thickness. As a reaction proceeds in each of the compartments, particularly where the reaction occurs adjacent the wafer surface, a product is produced which diffuses to the wafer surface 90. For example, in the case of a redox reaction, the redox products produced in the compartment migrate to the surface 90 and affect the photoresponse of the surface, either by reacting or creating a surface potential. In this manner, there is relatively little interference between the signals obtained from the various sites on the wafer surface 90 associated with an individual compartment 86. A transparent or semitransparent window 93 is separated from the silicon surface 90 by means of the supports 94. A small gap 95 is present between the surface 90 and the walls 88, so that the fluid can communicate between the compartments and provide for electrical communication between the silicon electrode 80 and platinum electrodes 97. The compartments 99 will be unaffected by changes in compartments 86, so as to maintain the solution composition substantially constant during the assay. An array of LEDs 92 provide for sequential illumination through compartments 86 to an associated site on the surface 90. The signal is read in association with the period of illumination.

In FIG. 4 is a partially broken away diagrammatic view looking downwardly on a device employing a plurality of channels. A housing 100 has a plurality of channels 102 having an inlet manifold 104 and an outlet manifold 106. A single reference electrode 108 is provided as well as a plurality of controlling counterelectrodes 110 deposited on the inner surface of the window 111. A plurality of inlet ports 112 associated with each of the channels is provided for introduction of the sample into a particular channel. The sample mixes with the assay medium from manifold 104 and the mixture proceeds through a channel 102. The base of the channel is a photoresponsive electrode 114. An air bubble may be introduced after the sample to separate the sample mixture from the following fluid. An LED array is provided, which is not shown, which illuminates each of the channels along its length, so that one or more sites in each channel 102 can be irradiated. A photoresponsive electrode 114 is in contact with the sample assay medium streams passing through channels 102 and filling the channels so as to be in contact with the counterelectrodes 108 and 110.

In this mode, one could employ a homogeneous assay technique employing an enzyme which catalyzes the reaction resulting in a change in pH or redox potential of the assay medium. The rate of the reaction in each channel can be determined by taking sequential readings as a function of time at the same or different points. The rate of reaction can be determined by making sequential readings as the assay medium traverses the channel at different points along the channel. Thus, the rate of change of enzymatic activity in each channel can be determined and related to the concentration of analyte in the sample assay medium. The continuous flow of assay medium through the channel can serve to wash the channel and restore the channel for the next determination. Alternatively, by employing various valves one can alternate medium with wash solution, so as to restore the channel to its original state.

FIG. 5 is a diagrammatic view of a photoresponsive surface having a plurality of sites which are insulated one from another, but connected to a common bus and having independent compartments for the assay medium. The device has a container 120 which is shown as having only one line of photoresponsive semiconductors 122. The photoresponsive semiconductors are in electrical contact with a common bus 124, connected to lead 126 for connection to an appropriate circuit. A plurality of tubes 130 connected to inlets 132 provide for introduction of solutions into the compartments 134. Each of the compartments is separated by dividers 136. The tubes 130 have three-way valves 140 so that the wash solutions or other common solutions may be introduced or removed by means of inlet port 142. By appropriate manipulation of the valves 134, the same solution may be introduced or removed from each of the compartments simultaneously, assuring uniformity. Individual sample inlets 144 are provided for each compartment, so that the sample solution is directly introduced into a compartment 134 without contamination from other samples. A common counterelectrode 146 is employed and introduced at a plurality of sites to provide for an average value. These electrodes are connected to the circuit, not shown, to which the common bus is connected. An LED array 150 is provided having individual LEDs 152 which can be controlled to sequentially illuminate the compartments in accordance with a predetermined schedule, so that the observed signal can be related to a specific compartment. Each of the photoresponsive devices 122 is coated with a specific binding layer indicated by the dark line 154. For the purposes of the following example, the layer would be a saccharide layer for which a specific lectin was available.

An assay could be carried out as follows: Using the manifold 156 the valves 140 would be arranged so that a solution containing an enzyme, such as acetylcholinesterase conjugated to lectin could be simultaneously introduced into each of the compartments through inlets 132. After a sufficient time for incubation the solution would be withdrawn through inlets 132 and each of the compartments washed with an appropriately buffered wash solution. Individual sample solutions would be prepared containing an unknown sample or a standard, antibody to an analyte, e.g., morphine, and a morphine conjugate to an acetylcholinesterase inhibitor, e.g., morphine fluorophosphonate, methyl, ethoxy, thiophosphates, etc. Also included would be an acetylcholinesterase substrate and the solution lightly buffered to pH 7. Each of the compartments would then be partially filled with the lightly buffered solution, whereupon introduction of the sample through sample inlets 144 and inlets 132 the compartments would overflow, so that there would be uniform electrical contact with the counter electrodes 146.

The hydrolysis of acetylcholine results in production of acetic acid, which would change the pH of the medium adjacent to the photoresponsive surface. The amount of enzyme which is inhibited would be directly proportional to the amount of analyte in the sample, since enzyme inhibitor conjugate bound to antibody to analyte would be inactive in inhibiting the enzyme. After sufficient time for reaction to occur to obtain a detectable signal at the concentration range of interest, the compartments would be sequentially irradiated and the signals detected by means of the circuit, not shown. After a sufficient time when one or more readings would have been made, the assay determination would be terminated by withdrawing the solutions from each of the compartments through inlets 132 and inlet port 142 by turning valves 134 to connect each of the inlets 132 with the inlet port 142. After removal of the assay media and washing the compartments, a concentrated saccharide solution would then be introduced into each of the compartments repetitively, until all of the enzyme had been removed from the surface. The compartments would then be washed with a wash solution to remove all of the unbound saccharide, followed by introduction of the enzyme-lectin conjugate to restore the compartment to its original state for performing an assay.

The following experiments were constructed to demonstrate the use of the device to monitor three different characteristics of fluid media: The first characteristic being pH, the second being the presence of molecules capable of participating in redox reactions, and the third being the presence of light-absorbing species in the illumination pathway. Evidence is also presented showing that signals are modified specifically by chemical species adjacent to the illuminated site of the silicon wafer and that the presence or absence of similar species at adjacent but non-illuminated sites have negligible effect.

Except where indicated otherwise, the experiments described in the following paragraphs employed the CAM-controlled device together with a single photoresponsive semiconductor electrode having two fluid-filled, open-ended channels adjacent to its surface. The semiconductor electrode is a 2-inch diameter P111 7-14 ohm "Pen Prime" boron-doped silicon wafer soldered to a copper wire, with electrical contact effected by use of an indium-gallium mixture. To construct the channels, the wafer is fixed to an optically clear garnet wafer by means of three strips of tape having adhesive on both sides and a thickness of 70μ. This dimension is then the depth of the channels, the other dimensions being 0.5 cm width and 3 cm length. The exposed garnet surface is then covered by optically opaque black electrical tape, except at two 25 mm$^2$ sites. These two transparent sites are each adjacent to one of the two channels and also to one of two LEDs. This configuration allows for site-specific (and channel-specific) illumination of the opposing continuous silicon wafer surface. The semiconductor electrode is positioned in such a way that the two channels both dip a few millimeters into the same bath of 40–50 ml 0.1M phosphate buffer, pH 6.7–6.8. The platinum electrode is either placed in this same bath or in an adjacent bath containing 40–50 ml 0.1M phosphate buffer to which is optionally added, particularly for redox measurements, $K_4[Fe(CN)_6]$ at 0.2 mM and $K_3[Fe(CN)_6]$ at 0.3 mM (approximately). In this latter mode, the bath containing the platinum electrode is connected to that containing the silicon electrode by means of a salt bridge of half-saturated KCl solution, solidified by 2% agar. The ionic redox couple facilitates reversibility of the platinum electrode, a feature which may be important to reduce drift and increase electrical stability for some applications.

In the mode described above, the applied potential is typically $-600$ mV to $-1000$ mV with the AC photoresponse fixed at a preselected value.

To demonstrate use of the device to sense pH, a series of six buffered salines was prepared with pH values (as determined using a Fisher Accumet pH meter, Model 620) of 4.0, 5.0, 6.0, 7.0, 8.0, 9.0. In all cases, the buffering species was at 0.01M and NaCl at 0.135M. For buffered salines having pH 4.0 and 5.0 the buffering agent was acetate; for buffered salines having pH 6.0 and 7.0 the buffering agent was phosphate; for buffered salines having pH 8.0 and 9.0 the buffering agent was TRIS. A channel adjacent to the silicon wafer was sequentially filled with each of the buffered salines and illuminated, as previously described, by an LED. The applied potential required to maintain a constant photoresponse was recorded. This applied potential is roughly proportional to pH, with a slope of $-40$ mV per pH unit. When the second channel was similarly illuminated and sequentially filled with buffered salines an essentially identical result was obtained. Changing the pH of the fluid in the non-illuminated channel does not affect the applied potential required to maintain a constant photoresponse when the illuminated site is maintained at a constant pH, i.e., the response is specific for the channel which is being illuminated and so can be used to monitor pH variation at different sites on the same wafer: selection being effected by varying the site of illumination.

When the device is maintained at constant applied potential with the monitored response being the amplitude of the alternating photoinduced current, analogous results are obtained on variation of pH at different sites on the wafer. For example, the fact that the photoresponsive electrode can sense pH gradients at its surface was further demonstrated using a fixed applied potential. An aqueous solution of 5% (w/w) gelatin was made in 0.15M NaCl. The gelatin was deposited to a depth of about 5 mm in a 100 mm diameter plastic Petri dish. One cm diameter circles of gelatin were cut out, soaked in buffers of pH 4.0, 7.0 or 10.0 overnight and then redeposited in their positions in the Petri dish. An array of six LEDs of equal light intensity were brought up to the bottom surface of the Petri dish, so as to match the gelatin cut-outs. The LEDs were pulsed at 100 Hz and the photoeffects were recorded for each of the six areas of defined pH, as described previously. The alternating current photoresponse readings for pH 4 were 0.55, 0.68 volts; pH 7, 0.20, 0.18 volts; and pH 10; 0.02, 0.02 volts as peak to peak value. A solution in an electrode well was provided in the Petri dish to be in electrical communicating relationship with the gelatin and was 0.15M NaCl.

Construction of a multiplicity of channels or compartments adjacent to the wafer facilitates comparison of one or more "experimental" samples with one or more "reference" samples. Using the two-channel silicon wafer/garnet wafer device, described previously, it is possible to monitor both channels on an essentially continuous basis through alternate illumination of the two sites described previously. The photoresponse as modified by the reference sample may be automatically subtracted from that modified by the experimental sample by sinusoidally illuminating both channels continuously and 180° out of phase and recording the amplitude of the alternating current using the circuit shown in FIG. 1, optionally with the reference and controlling electrodes shorted together. This technique has been used to monitor the growth of bacteria on the basis of their ability to reduce the pH of their surroundings. A nutrient solution comprising 0.85% NaCl, 0.75% glucose, and 0.25% peptone was used as the standard solution, and this nutrient medium containing $10^7$/cc cells of E. coli prepared for comparison. At about the same time, the nutrient solution was passed through the standard channel and the bacterial suspension passed through the sample channel. After 20 min it was noted that a substantial decrease in pH occurred as evidenced by a change in potential of 50 mV between 0 time and 20 min. Thus, the system could be employed to detect the presence of bacteria in a medium which should be otherwise free of bacteria or by employing antibodies to particular microorganisms, one could provide for specific binding of the microorganisms, followed by washing to remove non-specifically-bound microorganisms, and then determine whether there was any change in pH with time.

Similarly, the activity of an enzyme (penicillinase) which effects a pH reduction when it acts on its substrate (penicillin) was studied using the same technique. In this study, 10 μl of a solution containing various concentrations (<5 units/ml) of penicillinase in PBS was combined with 1 ml of a 1 mg/ml penicillin G in 10.5 mM PO$_4$, 0.15M NaCl, pH 8.3 solution and the mixture contacted with the photoresponsive surface of the device. The reference solution contained no penicillinase. The circuit of FIG. 1 was employed, except that the reference electrode and controlling electrode were shorted together. The limit of detection was about 0.25 units/ml of penicillinase, based on changes in electrical response resulting from changes in pH. However, when introduced at high concentrations (approximately 5 units/ml) the penicillinase became bound to the surface and the bound penicillinase could be used for the determination of the concentration of solutions of penicillin added subsequently. Denaturation and/or removal of the penicillinase could be achieved by treatment of the surface with 1N NaOH, followed by 1N HCl, followed by washing with PBS.

To demonstrate the use of the device to detect light-absorbing species in the illumination pathway, microscope slides were affixed to the garnet side of a silicon wafer/garnet wafer assembly using tape with adhesive on both sides. The tape was positioned in such a way that a second set of 70μ deep channels were constructed (between the garnet and the microscope slides) which exactly overlaid the first set of channels (between the silicon and garnet wafers). The first set (adjacent to the silicon wafer) were filled with phosphate-buffered saline at pH 6.8. Various concentrations of a green dye, Schilling Food Color (a mixture of FD&C yellow #5 and FD&C blue #1) were prepared and used to sequentially fill the second set of channels. The applied potential required to maintain a constant time dependent photoresponse, to illumination by LEDs with a 655 nm wavelength, was recorded (FIG. 6). Application of Beer's law indicated that the applied potential was linearly related to the incident light at the surface of the silicon wafer and thus could be used to measure the concentration of a light-absorbing species in the illumination pathway. Comparison of these results with those given by a Beckmann Spectrophotometer indicated that had the pathlength of the dye-containing channels been 1 cm (rather than 70μ) a change in concentration corresponding to an OD$_{655\ nm}$=1.00 (as measured on the spectrophotometer) would have given an applied voltage charge of 90 mV as measured using the described device.

To demonstrate the use of the device for measuring the concentration of oxidizing (electron accepting) molecules and monitoring redox reactions, the following experiments were performed. Reversibility of the platinum electrode was facilitated as previously described and the silicon wafer/garnet wafer assembly (having two channels) was employed. A redox solution was prepared which was 0.033M Fe(CN)$_6{}^{-4}$/Fe(CN)$_6{}^{-3}$, 0.1M NaCl, 0.014M phosphate. The redox solution was introduced into channels of the device described above. A plot of mvolts applied potential versus the log of the Fe$^{+2}$/Fe$^{+3}$ concentration ratio was plotted and gave a straight line with a slope of 49 mV/unit (FIG. 7). As previously described for pH determination, the response generated at the illuminated site is modified by the redox solution in the channel adjacent to that site, with negligible interference produced by the solution with a different $Fe^{+2}/Fe^{+3}$ value added to the parallel non-illuminated channel.

In further experiments the substance methylene blue (MB) was used as an electron-transfer agent communicating with the silicon wafer. Unless stated otherwise, the MB was at 5 μg/ml and the diluent was phosphate-buffered saline for these experiments. When MB at 5 μg/ml is introduced into a channel of the silicon wafer/garnet wafer assembly a transient (~30 sec) applied potential signal of about −90 mV is recorded. If NADPH at 1 mg/ml has previously been mixed with the MB solution and left for about 5 min (in a sealed container which includes little air), the recorded transient signal is about −8 mV. Use of varying concentrations of NADPH has shown that measurement of NADPH concentration is possible by means of this technique.

It is also possible to measure the concentration of the enzyme, horseradish peroxidase (HRPO), by a similar technique. Using MB at 5 μg/ml and $H_2O_2$ at 0.15%, together with various concentrations of HRPO (0.005 to 50 μg/ml), applied potential signals which were maintained at high values for several minutes were recorded. In a typical experiment, the maintained signal measured at 1 min after addition of the reagents to the device was −80 mV and −470 mV, respectively, for HRPO at 0.005 and 50 μg/ml (with intermediate applied potential values obtained for intermediate HRPO concentrations). In contrast, in the absence of HRPO, $MB + H_2O_2$ produces a transient 30 sec signal characteristic of MB alone which decays to the baseline value by 1 min after addition to the device.

If MB is added to milk, at a final concentration of 5 μg/ml, and the mixture introduced into the device, an elevated applied potential signal is maintained for many minutes. The amplitude of this maintained signal is significantly reduced by the presence of *E. coli* growing in the milk. This indicates that bacterial growth may be monitored by such a method. The milk had not changed pH, as monitored using a pH meter.

It is also possible to use a similar technique to measure the concentration of $H_2O_2$. In an experiment designed to illustrate this, MB and HRPO were used together, each at 5 μg/ml. Addition of $H_2O_2$ (at various concentrations) prior to introduction of the mixtures to the device, showed that the transient signal observed at 6 μM $H_2O_2$ (−150 mV) was about 50% greater than that observed in its absence (−90 mV). In the range 0-50 μM $H_2O_2$, transient signals are obtained with amplitudes which are approximately linear with $H_2O_2$ concentration.

A similar technique has been used to assay glucose. In this case, glucose (at various concentration) was introduced to the enzyme glucose oxidase (GO) at 5 μg/ml and left at room temperature for 40 min. At this time, MB and HRPO were added to give a final concentration of 5 μg/ml of each substance and the solutions were sequentially introduced into the device. With 1.55 μg/ml (−8 μM) glucose the transient applied voltage signal was about 50% greater than that observed in its absence.

As evidenced above, assays can be performed for the substrates of such enzymes as cholesterol oxidase, galactose oxidase, uricase, xanthine oxidase, etc., to a level of better than 10 μM, or the enzymes themselves may be the species assayed. While the enzymes indicated above are associated with $H_2O_2$ formation, other enzymes not involving the formation of $H_2O_2$ will also be assayable.

The photosignal from the redox pair is channel specific. Different redox compositions in different channels can be determined on a single monolithic surface, essentially simultaneously. It is also possible to measure one property in one channel, e.g., redox, and a different property in a different channel, e.g., pH.

It is evident from the above results, that the subject devices and methods provide for an accurate, rapid and efficient method for measuring a wide variety of materials in a medium capable of modulating an electrical photoresponse. The subject device can be adapted to be used with liquids, gels and solid materials. The device can be used for measuring a large number of samples substantially simultaneously, employing rapid readouts, allowing for redundancy, so as to ensure accurate results, and providing for concomitant standardization of determinations. The method can be used with a state (non-flowing) medium or a dynamic (flowing) medium. In addition, the method can be used for the determination of rates. Various types of separation techniques can be monitored or analyzed, such as electrophoresis, Southern blots, plaque formation, or the like, where specific sites can be defined in accordance with variations in signals and position on a surface.

Although the foregoing invention has been described in some detail by way of illustration and example for purposes of clarity of understanding, it will be obvious that certain changes and modifications may be practiced within the scope of the appended claims.

What is claimed is:

1. A photoresponsive device for making at different sites a plurality of determinations of a substance capable of modulating an electrical signal resulting from irradiation of a photoresponsive element, said device comprising:

a photoresponsive element having an irradiation receiving surface;

irradiation means for irradiating at least two sites on said irradiation receiving surface to provide distinguishable signals;

means for polarizing said photoresponsive element, said polarizing means connected to said photoresponsive element; and means for retaining media in which said substance is to be determined in photoresponsive modulating relationship to at least two sites; and means for measuring the potential of said polarizing means during irradiation of a site.

2. A photoresponsive device according to claim 1, wherein said photoresponsive element is a monolithic doped silicon semiconductor wafer.

3. A photoresponsive device according to claim 1, including a clear sheet in close spaced apart parallel juxtaposition to said irradiation receiving surface.

4. A photoresponsive device according to claim 1, wherein said irradiation means is an LED array programmed to provide regular light pulses.

5. A photoresponsive device according to claim 1, wherein a portion of said photoresponsive element is coated with a lipid bilamellar layer for contact with said media.

6. A photoresponsive device according to claim 5, wherein said lipid bilamellar layer is coated on said irradiation receiving surface and has a specific binding pair member bound to said layer.

7. A photoresponsive device according to claim 1, wherein said means for retaining media is a plurality of channels, each of said channels associated with an irradiation site.

8. A photoresponsive device according to claim 1, wherein said means for retaining media is a plurality of compartments, each of said compartments associated with an irradiation site.

9. A photoresponsive device for making a plurality of determinations of a substance in each of selected volumes, said substance being capable of modulating the electrical response resulting from irradiation at each of a plurality of sites related to each of said volumes, said sites being at the surface of a photoresponsive semiconductor, said device comprising:

a photoresponsive monolithic semiconductor element electrode having an irradiation receiving surface;

irradiating means for irradiating a plurality of said sites with light of energy of at least about the band gap energy of said element;

a counterelectrode;

polarizing means for polarizing said photoresponsive monolithic semiconductor element electrode in relation to said counterelectrode;

means for maintaining said photoresponsive monolithic semiconductor element electrode and said counterelectrode in electrically communicating relationship through an electrically responsive medium;

means for maintaining at least a portion of said electrically responsive medium in photoresponsive modulating relationship at each of said sites; and means connected to said counterelectrode and photoresponsive monolithic semiconductor element electrode for determining changes in polarization between said counterelectrode and photoresponsive monolithic semiconductor element electrode as a result of differences between said electrically responsive medium at a one of said sites and relating said change in polarization to the presence of said substance.

10. A photoresponsive device according to claim 9, wherein said polarizing means includes means for providing a potential to said counterelectrode; and said determining means includes means for passing a polarizing current through said photoresponsive monolithic semiconductor element electrode to return the potential between said photoresponsive monolithic semiconductor element electrode and said photoresponsive monolithic counterelectrode to a predetermined potential and means for measuring said polarizing current.

11. A photoresponsive device according to claim 10, wherein irradiating includes means for programming said light as regular pulses.

12. A photoresponsive device according to claim 10, wherein said means for maintaining at least a portion of said electrically responsive medium in photoresponsive modulating relationship at each of said sites comprises a plurality of elongated channels.

13. A photoresponsive device according to claim 10, wherein said means for maintaining at least a portion of said electrically responsive medium in photoresponsive modulating relationship at each of said sites comprises a plurality of compartments.

14. A photoresponsive device according to claim 9, including a clear sheet in facing relationship with said irradiation receiving surface.

15. A photoresponsive device according to claim 9, wherein said polarizing means reverse biases said photoresponsive monolithic semiconductor element electrode to inhibit current flow in said electrically responsive medium.

16. A method for substantially simultaneously determining a substance in a plurality of volumes of an electrically responsive medium, employing a photoresponsive element having a common lead through an electrical circuit to a counterelectrode, wherein said substance is capable of modulating the photoresponse of said photoresponsive element;

said method comprising:

directing said medium into photoresponsive modulating relationship with a photoresponsive surface of said photoresponsive element;

maintaining electrical communication between said photoresponsive element and said counterelectrode through an electrically responsive fluid or gel;

irradiating said surface at a plurality of sites in relation to individual volumes at different times in a predetermined sequence for short periods of time at each of said sites;

determining by means of said circuit the presence of said substance in each of said volumes by the effect of said substance on the electrical signal resulting from said irradiation.

17. A method according to claim 16, wherein said circuit includes means for polarizing said photoresponsive element in relation to said counterelectrode and means for measuring the current necessary to restore the level of polarization during irradiation of said surface.

18. A method according to claim 16, wherein said substance is a result of an enzymatic reaction.

19. A method according to claim 18, wherein said substance is a hydrated proton.

20. A method according to claim 16, wherein said photoresponsive element is a monolithic doped silicon wafer.

21. A method according to claim 16, wherein said volumes are portions of at least one stream.

22. A method according to claim 16, wherein each of said volumes is physically separated from the other volumes.

23. A method according to claim 16, wherein said substance is a light-absorbing substance.

24. A method according to claim 16, wherein said circuit maintains said photoresponsive element and counterelectrode at a predetermined potential difference and measures the current necessary to restore the potential difference upon irradiation of said surface.

25. A method for determining the presence of an analyte in a sample which is a member of a first specific binding pair consisting of ligand and receptor, said method employing:

(a) a photoresponsive electrode having an irradiation surface;

(b) a counterelectrode;

(c) an electrical circuit connecting said photoresponsive electrode and counterelectrode and maintaining said electrodes in a predetermined potential relationship;

(d) a binding surface for binding a member of a specific binding pair, which surface is said irradiation surface or a facing surface in close spaced apart juxtaposition to said irradiation surface; and (e) specific binding means for specifically binding one of said members of said first specific binding pair to said binding surface;

said method comprising:

combining assay components with said specific binding means, said assay components including a sample, a labeled specific binding pair member, which labeled specific binding pair member is a member of said first pair or capable of binding to, either directly or indirectly, a member of said first pair, wherein said label is a member of a system capable of modulating the electrical photoresponse of said photoresponsive electrode, and any additional members of said system;

irradiating a plurality of sites on said irradiation surface in relation to individual volumes of said combined components at different times in accordance with a predetermined schedule; and determining the electrical photoresponse as modulated by said system by means of said circuit as indicative of the presence of said analyte in said sample.

26. A method according to claim 25, wherein said photoresponsive semiconductor is a doped monolithic silicon wafer.

27. A method according to claim 26, wherein said specific binding means is a second ligand and receptor.

28. A method according to claim 27, wherein said second ligand and receptor are a saccharide and a lectin.

29. A method according to claim 27, wherein said second ligand and receptor are a ligand and a natural receptor.

30. A method according to claim 27, wherein said second ligand and receptor are hapten and its reciprocal antibody.

31. A method according to claim 26, wherein said label is an enzyme.

32. A method according to claim 31, wherein said enzyme catalyzes a reaction which produces a change in pH.

33. A method according to claim 31, wherein said enzyme produces a light-absorbing product.

34. A method for determining the presence of an enzyme substrate in a medium, wherein said enzyme substrate is a component of a system capable of modulating the electrical photoresponse of a photoresponsive electrode, said method employing:

(a) a photoresponsive semiconductor electrode having an irradiation surface;

(b) at least one counterelectrode;

(c) an electrical circuit connecting said photoresponsive semiconductor electrode and counterelectrode and maintaining said photoresponsive semiconductor electrode and counterelectrode in a predetermined potential relationship;

(d) a binding surface for binding said enzyme at a plurality of sites;

said method conprising:

contacting said enzyme at each of said sites with an aqueous medium containing said substrate and any additional components necessary for the enzymatic catalyzed reaction;

irradiating said sites on said irradiation surface at different times in accordance with a predetermined schedule; and determining the electrical photoresponse as modulated by said system by means of said circuit as a measure of the amount of said substrate present.

35. A method according to claim 34, where the reaction catalyzed by said enzyme results in a change in pH.

36. A method according to claim 34, wherein said reaction catalyzed by said enzyme results in a product capable of absorbing the irradiation light.

37. A method for determining the presence of one or more microorganisms in a medium, said method employing:

(a) a photoresponsive electrode having an irradiation surface;

(b) at least one counterelectrode;

(c) an electrical circuit connecting said photoresponsive electrode and counterelectrode and maintaining said photoresponsive electrode and counterelectrode in a predetermined potential relationship;

said method comprising:

contacting said medium at each of said sites under conditions where said microorganism remains viable and produces at least one metabolic product capable of modulating the photoresponse of said photoresponsive electrode;

irradiating said sites on said irradiation surface at different times in accordance with a predetermined schedule; and determining the electrical photoresponse as modulated by said metabolic products by means of said circuit as an indication of the presence of a microorganism.

38. A method according to claim 37, wherein said microorganism is bound by a specific receptor in juxtaposition to said site.

* * * * *